US00PP08758P

United States Patent [19]

VandenBerg

[11] Patent Number: Plant 8,758

[45] Date of Patent: May 31, 1994

[54] CHRYSANTHEMUM PLANT NAMED CREAM NICOLE

[75] Inventor: Cornelis P. VandenBerg, Salinas, Calif.

[73] Assignee: Yoder Brothers, Inc., Barberton, Ohio

[21] Appl. No.: 982,951

[22] Filed: Nov. 30, 1992

[51] Int. Cl.[5] ..... A01H 5/00

[52] U.S. Cl. ..... Plt./78

[58] Field of Search ..... Plt. 78, 77

[56] References Cited

U.S. PATENT DOCUMENTS

| | | | |
|---|---|---|---|
| 4616099 | 10/1986 | Sparkes | 47/58 |
| PLT 7790 | 2/1992 | VandenBerg | PLT/78 |
| PLT 7578 | 7/1991 | VandenBerg | PLT/78 |
| PLT 7577 | 7/1991 | VandenBerg | PLT/78 |
| PLT 6620 | 2/1989 | Mack, et al. | PLT/77 |
| PLT 6613 | 2/1989 | Duffett, et al. | PLT/77 |

OTHER PUBLICATIONS

Broertjes, et al., 1980, "A mutant of a mutant of a . . . Irradiation of progressive radiation-induced mutants in a mutation breeding programme with *C. morifolium*," Euphytica, 29:525-530.

Gosling, ed., 1979, "The Chrysanthemum Manual-6th edition", The National Chrysanthemum Society, London, Essex Telegraph Press, Ltd., pp. 329-336.

Broertjes, et al., 1978, "Application of Mutation Breeding Methods in the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of chrysanthemums", Euphytica, 15:156-162.

Dowrick et al., 1966, "The induction of mutations in Chrysanthemum using X- and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Cream Nicole particularly characterized by its flat capitulum form; decorative capitulum type; cream ray floret color; diameter across face of capitulum of 53 to 61 mm when fully opened; branching pattern is spreading and prolific, with 7 to 9 breaks after pinch when grown outside under natural daylength in fall flowerings, and 6 breaks after pinch when grown in 10 cm pots for spring flowerings; natural season flower date of August 12 to 18 when planting rooted cuttings on June 25 in Salinas, Calif., and September 14 to 21 when planting rooted cuttings June 15 in Hightstown, N.J.; flowering response of 45 to 46 days after rooting in no light/no shade programs in spring in Salinas, Calif.; plant height of 20 to 25 cm when grown in fall under natural daylength with no growth regulators, and 13 to 15 cm when grown in 10 cm pots in spring with 1 application of 2500 ppm B-9 SP; and durable, uniform performance.

1 Drawing Sheet

The present invention comprises a new and distinct cultivar of Chrysanthemum, botanically known as *Dendranthema grandiflora*, and referred to by the cultivar name Cream Nicole.

Cream Nicole, identified as 8417 (85-033A01), is a product of a mutation induction program. The new cultivar was discovered and selected by Cornelis P. VandenBerg on Nov. 13, 1989, in a controlled environment in Salinas, Calif. as one flowering plant within a flowering block established as rooted cuttings from stock plants which had been exposed as unrooted cuttings to an X-ray source of 1500 rads in Fort Myers, Fla. on Jun. 8, 1989. The irradiated parent cultivar was the cultivar identified as Nicole, disclosed in U.S. Plant Pat. No. 7,517. Nicole is described as a spray pot mum and garden mum with a white floret color and a light yellow center of capitulum; diameter across face of capitulum of 44 to 64 mm when fully opened; spreading and prolific branching pattern, with 7 to 9 branches after pinch; average natural season flower date of August 13 to 26 in Salinas, Calif. and September 16 to 27 in Hightstown, N.J.; photoperiodic flowering response to short days in photoperiodic controlled flowering programs of 45 to 49 days; and durable, uniform performance. The above description of Nicole has a slightly wider range of values than disclosed in U.S. Plant Pat. No. 7,517 for Nicole, based on continued flower trials after the application for Nicole was filed.

The irradiation program resulting in Cream Nicole had as its primary objective the expansion of color ranges of the parent cultivar Nicole. The irradiation program comprised irradiating cuttings of the parent cultivar at irradiation levels of 1500, 1750 and 2000 rads. A total of 1412 cuttings harvested from a total of 225 irradiated plants were planted on September 11, September 4 and August 21, 1989, respectively. Of these, 23 initial selections were made, which selections were then revegetated and reflowered. Four consecutive flowerings resulted in discarding 20 of the original 23 selections on Aug. 29, 1990. Two selections were maintained as PIs (Possible Introductions) and trialed for one year, ultimately resulting in the decision to introduce the selection 8417 as Cream Nicole and selection 8424 as Yellow Nicole. Yellow Nicole is disclosed in applicant's pending application Ser. No. 07/981,220.

The first act of asexual reproduction of Cream Nicole was accomplished when vegetative cuttings were taken from the original selection in December 1989 in a controlled environment in Salinas, Calif., by technicians working under superivision of Cornelis P. VandenBerg.

Horticultural examination of controlled flowerings of successive plantings has shown that the unique combination of characteristics as herein disclosed for Cream Nicole are firmly fixed and are retained through successive generations of asexual reproduction.

Cream Nicole has not been observed under all possible enviornmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Highstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial practice for small pot spring garden mum production.

The following traits have been repeatedly observed and are determined to be basic characteristics of Cream Nicole, which, in combination, distinguish this Chrysanthemum as a new and distinct cultivar:

1. Flat capitulum form.
2. Decorative capitulum type.
3. Cream ray floret color.
4. Diameter across face of capitulum of 53 to 61 mm when fully opened.
5. Branching pattern is spreading and prolific, with 7 to 9 breaks after pinch when grown outside under natural daylength in fall flowerings, and 6 breaks after pinch when grown in 10 cm pots for spring flowerings.
6. Natural season flower date of August 12 to 18 when planting rooted cuttings on June 25 in Salinas, Calif., and September 14 to 21 when planting rooted cuttings June 15 in Hightstown, N.J.
7. Flowering response of 45 to 46 days after rooting in no light/no shade programs in spring in Salinas, Calif.
8. Plant height of 20 to 25 cm when grown in fall under natural daylength with no growth regulators, and 13 to 15 cm when grown in 10 cm pots in spring with 1 application of 2500 ppm B-9 SP.
9. Durable, uniform performance.

The accompanying photographic drawing is a color photograph of Cream Nicole grown as a pinched garden mum under natural season outside conditions in Salinas, Calif., with the colors being as nearly true as possible with illustrations of this type.

Of the commercial cultivars known to the inventor, the most similar in comparison to Cream Nicole is the parent cultivar Nicole. In the above description of Cream Nicole the ranges of values for Cream Nicole are much narrower than the ranges of values given for Nicole. This is based on the fact that Nicole was flowered over many years, while Cream Nicole was flowered over a period of only one and a half years. Most traits of Cream Nicole are similar to those of Nicole, except for the ray floret color. The ray floret color of Cream Nicole is cream, while the ray floret color of Nicole is white with a light yellow center of capitulum. In addition, in several flowerings Cream Nicole has been 2 to 4 days earlier in natural season flowerings when compared with Nicole. In most flowerings Cream Nicole had approximately 3 cm shorter plants at a time of flowering when compared with Nicole, and 3–4 mm smaller diameter flowers.

In comparison with Yellow Nicole, Cream Nicole has a 3–4 mm smaller diameter of capitulum and an approximately 3 cm shorter plant height.

In the following description color references are made to The Royal Horticultural Society Colour Chart. The color values were determined on plant material grown as a pinched garden mum grown under natural season outside conditions in Salinas, Calif. on Aug. 14, 1992.

Classification:

*Botanical.*—*Dendranthema grandiflora* cv Cream Nicole.

*Commercial.*—Flat decorative spray pot mum and garden mum.

I. INFLORESCENCE

A. Capitulum:

*Form.*—Flat.

*Type.*—Decorative.

*Diameter across face.*—53 to 61 mm when fully opened.

B. Corolla of ray florets:

*Color (general tonality from a distance of three meters).*—Cream.

*Color (upper surface).*—8 C, maturing on outer petals to 8D. Center of capitulum is slightly darker cream to light yellow, closest to 8B.

*Color (under surface).*—8D.

*Shape.*—Flat, straight, oblong.

C. Corolla of disc florets: Not present.

D. Reproductive organs:

*Androecium.*—None.

*Gynoecium.*—Present on ray florets.

PLANT

A. General appearance:

*Height.*—20 to 25 cm when grown in fall under natural daylength with no growth regulators, and 13 to 15 cm when grown in 10 cm pots in spring with 1 application of 2500 ppm B-9 SP.

*Branching pattern.*—Spreading and prolific, with 7 to 9 breaks after pinch when grown outside under natural daylength in fall flowerings, and 6 breaks after pinch when grown in 10 cm pots for spring flowerings.

B. Foliage:

*Color (upper surface).*—147A.

*Color (under surface).*—147B.

*Shape.*—Lobed, slightly serrated.

I claim:

1. A new and distinct Chrysanthemum plant named Cream Nicole, as described and illustrated.

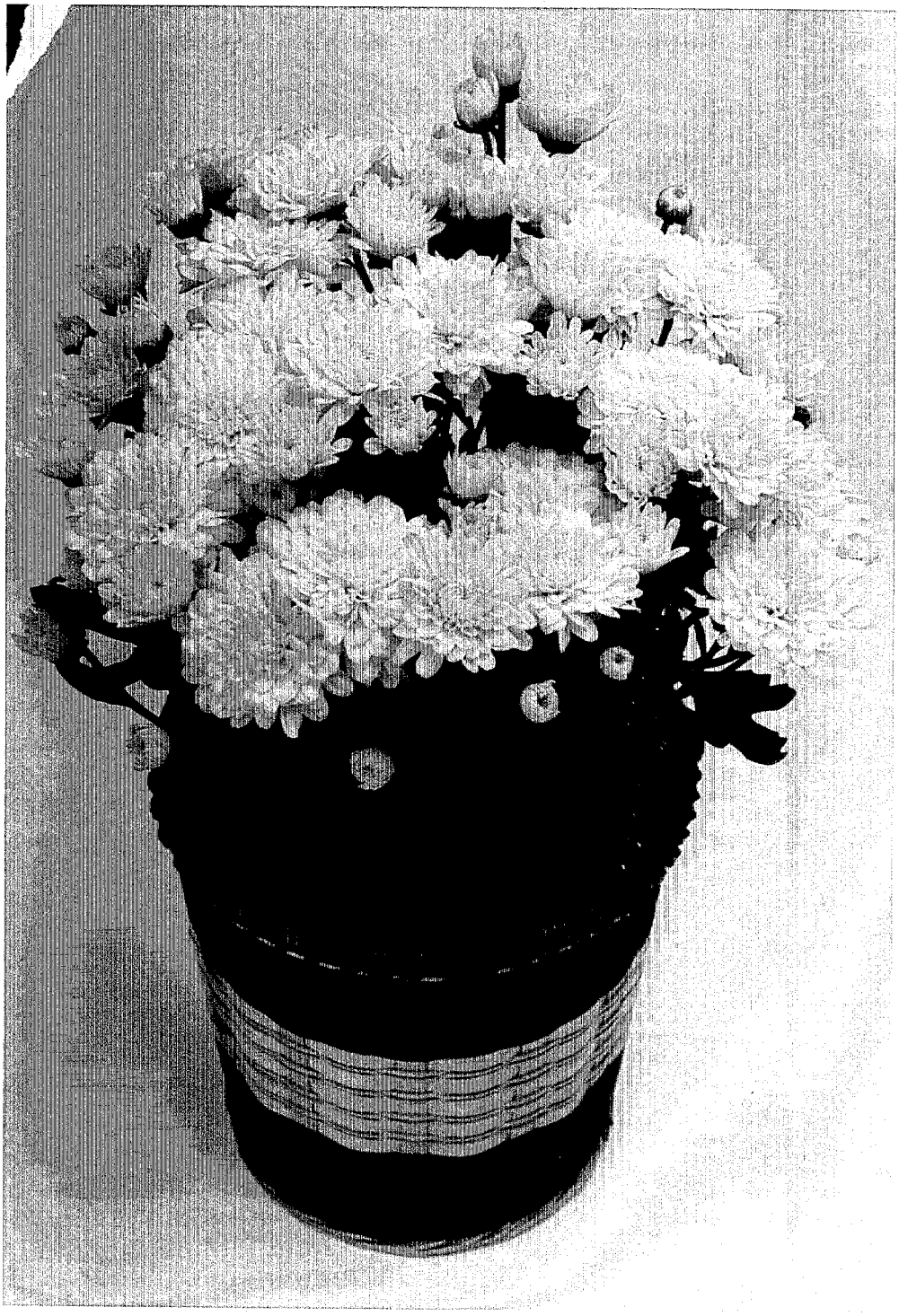

* * * * *